(12) United States Patent
Parvataneni et al.

(10) Patent No.: US 10,383,872 B2
(45) Date of Patent: Aug. 20, 2019

(54) PHARMACEUTICAL COMPOSITIONS COMPRISING PHENYLAMINOPYRIMIDINE DERIVATIVE

(71) Applicant: NATCO PHARMA LTD, Hyderabad (IN)

(72) Inventors: Durga Maheswari Parvataneni, Hyderabad (IN); Mitrabhanu Mohanty, Hyderabad (IN); Venkata Satyanarayana Appadwedula, Hyderabad (IN); Kali Satya Bhujanga Rao Adibhatla, Hyderabad (IN); Venkaiah Chowdary Nannapaneni, Hyderabad (IN)

(73) Assignee: NATCO PHARMA LTD, Hyderabad (IN)

( * ) Notice: Subject to any disclaimer, the term of this patent is extended or adjusted under 35 U.S.C. 154(b) by 0 days.

(21) Appl. No.: 16/062,320

(22) PCT Filed: Jan. 30, 2016

(86) PCT No.: PCT/IN2016/050035
§ 371 (c)(1),
(2) Date: Jun. 14, 2018

(87) PCT Pub. No.: WO2017/103941
PCT Pub. Date: Jun. 22, 2017

(65) Prior Publication Data
US 2019/0015412 A1   Jan. 17, 2019

(30) Foreign Application Priority Data
Dec. 18, 2015   (IN) ............................ 6951/CHE/2015

(51) Int. Cl.
| | | |
|---|---|---|
| *A61K 31/506* | (2006.01) |
| *A61P 35/02* | (2006.01) |
| *A61K 9/16* | (2006.01) |
| *A61K 9/19* | (2006.01) |
| *A61K 9/00* | (2006.01) |
| *A61K 9/14* | (2006.01) |
| *A61K 9/20* | (2006.01) |
| *A61K 9/48* | (2006.01) |

(52) U.S. Cl.
CPC .......... *A61K 31/506* (2013.01); *A61K 9/0095* (2013.01); *A61K 9/146* (2013.01); *A61K 9/1635* (2013.01); *A61K 9/1641* (2013.01); *A61K 9/1652* (2013.01); *A61K 9/19* (2013.01); *A61K 9/2027* (2013.01); *A61K 9/2054* (2013.01); *A61K 9/4866* (2013.01); *A61P 35/02* (2018.01)

(58) Field of Classification Search
None
See application file for complete search history.

(56) References Cited

U.S. PATENT DOCUMENTS

| 9,895,367 | B2 * | 2/2018 | Parvataneni ......... A61K 9/4858 |
| 2007/0232633 | A1 | 10/2007 | Kompella et al. |
| 2008/0306100 | A1 | 12/2008 | Kompella et al. |
| 2009/0227611 | A1 | 9/2009 | Kompella et al. |
| 2013/0338180 | A1 | 12/2013 | Parvataneni et al. |

FOREIGN PATENT DOCUMENTS

WO   2012/120328 A1   9/2012

OTHER PUBLICATIONS

International Search Report and Written Opinion dated Jul. 28, 2016 from International Application No. PCT/IN2016/050035, 10 pages.
Extended European Search Report dated Jul. 9, 2019 from European Application No. 16875074.3, 7 pages.
Leuner et al., "Improving drug solubility for oral delivery using solid dispersions", European Journal of Pharmaceutics and Biopharmaceutics, vol. 50, No. 13, Jul. 3, 2000, pp. 47-60.
Vasconcelos et al., "Solid dispersions as strategy to improve oral bioavailability of poor water soluble drugs", Drug Discovery Today, vol. 12, Nos. 23/24, Dec. 2007, pp. 1068-1075.

* cited by examiner

*Primary Examiner* — Brian J Davis
(74) *Attorney, Agent, or Firm* — MH2 Technology Law Group, LLP

(57) ABSTRACT

An oral pharmaceutical formulation containing an effective amount of NRC-AN-019 including its pharmaceutically acceptable salts and polymorphs thereof, by dispersing in a polymer system in a final state of subdivision to enhance oral bioavailability. It also relates to processes for the preparation of such compositions and using those compositions for the treatment of Chronic Myeloid Leukemia and other tumors such as head and neck cancer, prostate cancer and the like.

19 Claims, 3 Drawing Sheets

PHARMACEUTICAL COMPOSITIONS COMPRISING PHENYLAMINOPYRIMIDINE DERIVATIVE

CROSS-REFERENCE TO RELATED APPLICATIONS

This application is a U.S. National Stage application of PCT/IN2016/050035 filed 30 Jan. 2016, which claims priority to Indian Application No. 6951/CHE/2015 filed 18 Dec. 2015, the entire disclosures of which are hereby incorporated by reference in their entireties.

FIELD OF THE INVENTION

The present invention pertains to an oral formulation of a new chemical entity containing phenylaminopyrimidine derivative designated as development code NRC-AN-019 including its pharmaceutically acceptable salts and polymorphs. The invention also relates to processes for the preparation of such compositions and application of the compositions for the treatment of hyper proliferative disorders such as cancer.

BACKGROUND

NRC-AN-019 chemically known as (3,5-Bis trifluoromethyl)-N-[4-methyl-3-(4-pyridin-3-yl-pyrimidin-2-yl-amino)phenyl]benzamide, is a phenylaminopyrimidine derivative and it has the following structural formula.

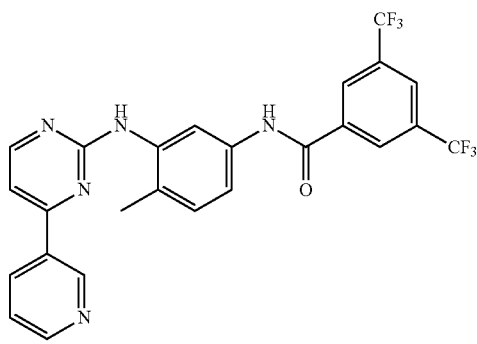 [SMILES: Cc1ccc(NC(=O)c2cc(C(F)(F)F)cc(C(F)(F)F)c2)cc1Nc1nccc(-c2cccnc2)n1]

NRC-AN-019 is herein incorporated by reference in its totality which exhibits a melting point range between 248-252° C. It shows poor aqueous solubility at physiological pH (0.0066 mg/mL at pH 1.2, 0.0002 mg/mL at pH 2.0 and below detection limit at pH 3.0, 4.0, 5.0, 6.0, 6.8, 7.0, 7.5, 8.0 and water) and consequently resulting in very low oral absorption. Its molecular formula is $C_{25}H_{17}F_6N_5O$ and its relative molecular mass is 517.44.

It has received "orphan drug designation" from the United States Food and Drug Administration (USFDA) for three indications—glioma (brain tumor), pancreatic cancer and chronic myelogenous leukemia (CML). NRC-AN-019 is a protein-tyrosine kinase inhibitor; it inhibits the abnormal functioning of BCR-ABL tyrosine kinase; Abelson (ABL) tyrosine kinase gene at chromosome 9 and the break point cluster (BCR) gene at chromosome 22, which is produced by the Philadelphia chromosome abnormality found in CML. NRC-AN-019 inhibits cell proliferation and induces apoptosis (programmed cell death) in the BCR-ABL cell lines and in the leukemic cells generated by CML. There has been a great deal of interest in understanding the role of tyrosine-specific protein kinases encoded by the transforming viruses and their normal cellular homologues and exploring their potential as therapeutic targets. Thus, BCR-ABL tyrosine kinase inhibitors have started era of molecular targeted therapy and marked a great milestone in cancer drug discovery.

Novel phenylaminopyrimidine derivatives have been disclosed as inhibitors of BCR-ABL kinase for the therapy of CML in US2007/0232633. The novel intermediates which are useful for the preparation of novel phenylaminopyrimidine derivatives have also been disclosed in the aforementioned patent application. This U.S. Patent application particularly describes novel phenylaminopyrimidine derivatives which can be used in the therapy of CML with pharmaceutically acceptable carriers that are suitable for topical, enteral, for example oral or rectal, or parenteral administration and may be inorganic or organic, solid or liquid. In addition to the active ingredient(s), the pharmaceutical compositions of the mentioned invention may contain one or more excipients or adjuvants. Example 14 of the said patent application discloses capsule formulations, comprising active compounds which are prepared by the process described in the examples 1 and 3 utilizing lactose, polyvinylpyrrolidone, talc, sodium lauryl sulfate, crospovidone and magnesium stearate as excipients. The capsule formulation disclosed in the said patent application was found to have very poor absorption characteristics. Polymorphic forms of NRC-AN-019 have been disclosed in US2008/0306100 and US2009/0227611.

US Patent Application No. US2013/0338180 discloses an oral solution comprising an effective amount of NRC-AN-019 including its pharmaceutically acceptable salts and polymorphs thereof which is intended for self-emulsification upon its contact with the gastro-intestinal fluid. In accordance with the aforementioned oral solution, bioavailability improvement was achieved.

Generally, oral solid dosage forms provide lower oral absorption than oral solution but contrary to that in view of patient compliance, solid dosage forms are generally preferred. Therefore, suitable solid dosage forms have been contemplated to obtain oral absorption of NRC-AN-019 that is as close as possible to the bioavailability obtained from oral solution. On account of patient non-compliance, a need arose to develop an orally administrable formulation for increasing the bioavailability of this novel phenylaminopyrimidine derivative with better patient acceptability.

The oral drug administration is the most generally accepted route of administration for treating diseases. Hydrophobic drugs exhibit poor solubility and release rate when administered as conventional tablets or capsules and thus exhibit lower bioavailability.

NRC-AN-019 is practically insoluble in water. It is soluble in dimethylformamide, dimethylacetamide and dimethyl sulfoxide. NRC-AN-019 presents specific difficulties in relation to solubility and its formulation development. Oral absorption of such insoluble drugs is the key point to be considered in solving the problem of low bioavailability.

The above mentioned problems have been solved by preparing a pharmaceutical composition comprising NRC-AN-019 and at least one polymeric matrix agent in the form of solid dispersion, wherein said solid dispersion can be directly used in the process of the preparation of pharmaceutical composition.

OBJECT OF THE INVENTION

It is an object of the invention to provide an oral pharmaceutical composition comprising NRC-AN-019 or, salts or, polymorphs thereof and at least one polymeric matrix agent in the form of solid dispersion.

It is further object of the invention to provide solid oral compositions comprising NRC-AN-019 or, salts or, polymorphs thereof and at least one polymeric matrix agent in the form of solid dispersion.

It is further object of the invention to provide oral pharmaceutical composition comprising NRC-AN-019 or, salts or, polymorphs thereof and at least one polymeric matrix agent in the form of solid dispersion, wherein NRC-AN-019 and the polymeric matrix agent are present in a homogeneous, molecularly disperse mixture.

It is further object of the invention to provide a method of treating CML and some other tumors such as head and neck cancer, prostate cancer and the like in patient by administering to said subject an oral pharmaceutical composition comprising NRC-AN-019 or, salts or, polymorphs thereof and at least one polymeric matrix agent in the form of solid dispersion.

It is further object of the invention to provide an oral pharmaceutical composition comprising NRC-AN-019 or, salts or, polymorphs thereof and at least one polymeric matrix agent in the form of solid dispersion, wherein the said oral pharmaceutical composition is stable throughout the shelf life in terms of physicochemical attributes.

It is further object of the invention to provide processes that stabilize the amorphous form of NRC-AN-019.

It is further object of the invention to provide a pharmaceutical composition with improved patient compliance comprising NRC-AN-019 or, salts or, polymorphs thereof and at least one polymeric matrix agent in the form of solid dispersion Embodiments of the present invention may include one or more of the following features for example the pharmaceutical composition may further include one or more pharmaceutically acceptable excipients. The pharmaceutical acceptable excipients may include diluents, disintegrants, surfactants, binders, lubricants, glidants, plasticizers, antitacking agents, polymers, opacifying agents, sweeteners/taste masking agents, colorants, flavors and the like.

STATEMENT OF INVENTION

Accordingly, the present invention provides a pharmaceutical oral formulation containing NRC-AN-019 including its pharmaceutically acceptable salts and its polymorphs thereof and a process for its preparation of solid dispersion so as to achieve effective therapy against CML and other tumors such as head and neck cancer, prostate cancer and the like.

DETAILED DESCRIPTION OF THE INVENTION

Figure 1:
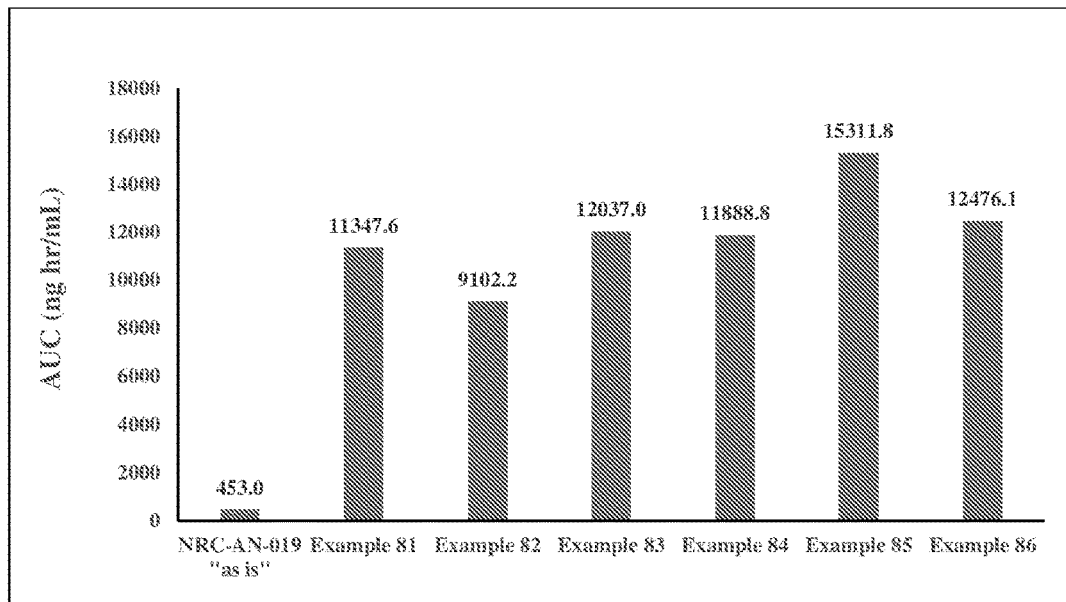
FIG. 1 illustrates the area under the curve in albino wistar rats after oral administration of NRC-AN-019 "as is" and different solid dispersions in accordance with the invention.

The inventors of the present invention have found that the solubility and bioavailability of NRC-AN-019 can be enhanced by the present invention. The present invention provides an oral pharmaceutical composition comprising therapeutically effective amount of phenylaminopyrimidine derivative i.e., (3,5-Bis trifluoromethyl)-N-[4-methyl-3-(4-pyridin-3yl-pyrimidin-2-yl-amino)phenyl]benzamide (NRC-AN-019) including its pharmaceutically acceptable salts and polymorphs thereof and at least one polymeric matrix agent in the form of solid dispersion. The term 'NRC-AN-019' is used in broad sense to include not only the NRC-AN-019 per se but also its pharmaceutically acceptable salts, solvates, hydrates, enantiomers, derivatives, polymorphs and prodrugs thereof and their crystalline and amorphous forms. The term "pharmaceutically acceptable" refers to those compounds, materials, compositions and/or dosage forms, which are within the scope of sound medical judgement, suitable for contact with the tissues of mammals, especially humans, without excessive toxicity, irritation, allergic response and other problem complications commensurate with a reasonable benefit/risk ratio.

The solid dispersion of NRC-AN-019 and polymeric matrix agent may contain additional pharmaceutically acceptable excipients such as carriers, fillers, surfactants, crystallization inhibitors, thickening agents, disintegrants, plasticizers, defoamers, antioxidants, stabilizers, glidants and lubricants. In an embodiment, the polymeric matrix agent is ionic polymer or a nonionic polymer or combinations thereof. The ionic polymer include methacrylic acid copolymers, cellulosic polymers, carboxyvinyl polymer, vinyl acetate polymers or combinations thereof.

In certain embodiments, methacrylic acid copolymers may be Eudragit® L 100, Eudragit® L 12.5, Eudragit® 12.5 P (commonly referred as poly(methacrylic acid, methyl methacrylate)); Eudragit® S 100, Eudragit® S 12.5, Eudragit® S 12.5 P (commonly referred as poly(methacrylic acid, methyl methacrylate)); Eudragit® L 100-55, Acryl-EZE® 93A, Acryl-EZE® MP, Eudragit® L 30 D-55, Eudragit® L 100-55, Eastacryl® 30D, Kollicoat® MAE 30 DP, Kollicoat® MAE 100 P (commonly referred as poly (methacrylic acid, ethyl acrylate)); Eudragit® E 100, Eudragit® E 12.5, Eudragit® E PO (commonly referred as poly(butyl methacrylate, (2-dimethylaminoethyl) methacrylate, methyl methacrylate)); Eudragit® FS 30 D (commonly referred as poly(methyl acrylate, methyl methacrylate, methacrylic acid)); Eudragit® RL 100, Eudragit® RL PO, Eudragit® RL 30 D, Eudragit® RL 12.5 (commonly referred as poly(ethyl acrylate, methyl methacrylate, trimethylammonioethyl methacrylate chloride)); Eudragit® RS 100, Eudragit® RS PO, Eudragit® RS 30 D, Eudragit® RS 12.5

(commonly referred as poly(ethyl acrylate, methyl methacrylate, trimethylammonioethyl methacrylate chloride)) and combinations thereof. Preferably, the methacrylic acid copolymer is poly (methacrylic acid, methyl methacrylate) and poly(methacrylic acid, ethyl acrylate).

In certain embodiments, the cellulosic polymers may be cellulose acetate phthalate (CAP), cellulose acetate butyrate, hypromellose acetate succinate (HPMCAS), hypromellose phthalate (HPMCP), carboxymethyl cellulose or, a salt thereof (e.g. a sodium salt such as sodium carboxymethyl cellulose), cellulose acetate trimellitate, hydroxypropyl cellulose acetate phthalate, hydroxypropyl methyl cellulose acetate phthalate and methylcellulose acetate phthalate.

In an embodiment, pH dependent enteric polymer is an anionic polymer which is soluble at a pH above 5.2 and practically insoluble at a pH below 5.2.

The nonionic polymer include but not limited to 2-hydroxypropyl ether, cellulose hydroxypropyl methyl ether, polyvinyl alcohol, α-Hydro-o-hydroxypoly(oxy-1,2-ethanediyl), polyvinylpyrrolidone, vinyl pyrrolidone/vinyl acetate copolymer, polyalkylene glycol (i.e. polyethylene glycol), hydroxyalkyl cellulose (i.e. hydroxypropyl cellulose, hydroxyethyl cellulose), hydroxyalkyl methyl cellulose (i.e. hydroxy propyl methyl cellulose), ethyl cellulose, polyvinyl cellulose, polyvinyl acetate, vinyl alcohol/vinyl acetate copolymer, polyglycolized glycerides, polydextrin, dextrin, proteins, polyacrylamides, N-(2-Hydroxypropyl) methacrylamide, polyoxazoline, polyphosphates, polyphosphazenes, natural water soluble polymers like pectins, xanthan gum, chitosan derivatives, chitin, dextran, carrageenan, guar gum, alginic acid, polyethylene oxide, polycarbophil, 1-Ethenyl-2-pyrrolidinone homopolymer, hyaluronic acid, albumin, starch or starch based derivatives, sugar and/or sugar alcohol and/or cyclodextrin, for example sucrose, lactose, fructose, maltose, raffinose, sorbitol, lactitol, mannitol, maltitol, erythritol, inositol, trehalose, isomalt, inulin, maltodextrin, β-cyclodextrin, hydroxypropyl-β-cyclodextrin, sulfobutyl ether β-cyclodextrin (sodium) or, combination thereof.

The pharmaceutical composition of the present invention comprises NRC-AN-019 in an amount of about 0.1% by weight to about 99.9% by weight, preferably in an amount of about 0.5% by weight to about 30% by weight and more preferably in an amount of about 0.75% by weight to about 20% by weight, relative to the total weight of the composition.

The polymeric matrix agent in the pharmaceutical composition of the present invention comprises in an amount of about 0.1% by weight to about 99.9% by weight, preferably about 5% by weight to about 95% by weight and more preferably about 10% by weight to about 90% by weight based on the total weight of the composition.

In an embodiment, the ratio of NRC-AN-019 and polymeric matrix agent in the solid dispersion is from about 1:0.1 to about 1:10, preferably from about 1:0.5 to about 1:9, more preferably, from about 1:1 to about 1:8.

In some embodiments, NRC-AN-019 is present in the complex in the form of a tosylate salt, mesylate salt, sulfosuccinate salt, hydrochloride salt and the like with the further inclusion of a pharmaceutically acceptable carrier. The salts are generated in-situ in the form of drug polymer complex to formulate the salt in an amorphous or, partially amorphous or, crystalline solid dispersions form.

In an embodiment, NRC-AN-019 in the present invention is in the form of crystalline or amorphous or combinations thereof. Preferably in amorphous form.

In the development of amorphous solid dispersions, manufacturing process may lead to small seed crystals which may further result in the nucleation process affecting the dissolution and bioavailability. Thus, inhibition of this nucleation is essential for any amorphous solid dispersion and it greatly depends upon stabilization aspects of the formulation. Solid dispersions are high energy formulations and possess high risk of re-crystallization. The rationale arises in understanding the specific interactions involved in the formulation of solid dispersions. The improvement with respect to solubility and bioavailability during the shelf life can be accomplished with the development of stable amorphous or, partially amorphous or, crystalline solid dispersions. The crystallization inhibitors inclusion in the solid dispersion results in arresting or, prolonging the onset of crystallization. In some embodiments, the nonionic polymer used, function as anti-crystallizing agent which prevent the crystallization behavior of NRC-AN-019.

The solid dispersion of the present invention is prepared according to the methods known in the art for the preparation of solid dispersions such as solvent controlled precipitation, solvent evaporation, lyophilization, pH controlled precipitation, hot melt extrusion and supercritical fluid technology.

Preferably, the solid dispersion of the present invention is prepared by solvent controlled coprecipitation.

Preferably, the solid dispersion may be obtained by solvent controlled co-precipitation, which comprises dissolving NRC-AN-019 and at least one polymeric matrix agent in suitable organic solvent followed by spraying the resultant solution in to anti-solvent. NRC-AN-019 and the polymeric matrix agent simultaneously precipitate out to form a molecular solid dispersion containing NRC-AN-019 embedded in the polymer system. The co-precipitate which is obtained can be isolated by using traditional methods like centrifugation, filtration, washing, delumping and drying. Drying can be done in tray dryer, fluid bed dryer, oven or vacuum. The resulting solid mass is either milled, pulverized or, micronized to a very fine powder.

A solvent suitable for dissolving NRC-AN-019 and polymeric matrix agent in solvent evaporation and solvent controlled co-precipitation include alcohols (e.g. methanol, ethanol, n-propanol, isopropanol, and butanol), ketones (e.g. acetone, methyl ethyl ketone and methyl isobutyl ketone), esters (e.g. ethyl acetate and propyl acetate), dimethylformamide, dimethylacetamide, dimethyl sulfoxide, acetonitrile, methylene chloride, chloroform, hexane, toluene, tetrahydrofuran, cyclic ethers, and 1,1,1-trichloroethane or, mixtures thereof.

The anti-solvent include, but not limited to, water, aqueous buffers, hydrochloric acid, ethyl acetate, toluene, methylene chloride, acetonitrile and the combination thereof. Preferably, the antisolvent used in the process is diluted hydrochloric acid.

Solid dispersions of NRC-AN-019 were also prepared by employing different technology to evaluate their application in the formulation development of the solid dispersions of NRC-AN-019.

pH controlled precipitation involves the micro precipitation of NRC-AN-019 in a polymer matrix which either gets dissolved at high pH and precipitates out at low pH or which gets dissolved at low pH and precipitates out at high pH. The process in the present invention involves dissolving of NRC-AN-019 and the polymer system in the organic phase such as dimethylformamide, dimethylacetamide (DMA), dimethyl sulfoxide, N-Methyl-2-pyrrolidone, acetone, ethanol or combination thereof. The pH of the solution is then lowered by adding an acid to dissolve NRC-AN-019 in the solvent phase. Precipitation of drug-polymer complex results with the increase in pH of the solution. This results in the formation of solid dispersion of NRC-AN-019 in the polymer matrix.

Hot melt extrusion involves the process of usage of heat to transform NRC-AN-019 along with the polymers into homogenously mixed mass that is, solid dispersion. The homogenous mass transformed into "fluid-like state" allows intimate and homogeneous mixing by the high shear of extruder screws. The intimately mixed hot mass, that is, solid dispersion, is extruded through the die opening. The extruded hot strands were molded and precisely cut into unit dosage forms using additional accessories. Alternatively, they are cooled, sized and encapsulated or compressed into tablets.

Supercritical fluid technology involves the rapid expansion of supercritical solutions during which the super critical fluid is diffused through a bed of solid solute (i.e., extractor) and the solid solute dissolves in it. NRC-AN-019 and the polymers are dissolved in liquid nitrogen or liquid carbon dioxide. The supercritical fluid was then removed by evaporation leaving NRC-AN-019 micro-precipitated in the matrix formed by the polymer.

The solid dispersions described herein is further blended with different excipients like diluents, binders, drug stabilizers, disintegrants, glidants, lubricants, release rate modifiers, antioxidants, fillers, surface active agents, drug complexing agents, solubilizers and pH modifiers (e.g. acids, bases, or buffers), coatings, colorants, sweeteners, flavoring agents to convert into suitable dosage forms like powders or granules tablets, capsules, or pills that can be taken orally either dry or reconstituted by addition of water to form a paste, slurry, suspension, or solution.

Examples of other matrix materials, fillers or diluents include starches, lactose, cellulose derivatives, lactose, mannitol, xylitol, microcrystalline cellulose, salts of calcium, potassium sodium, magnesium confectioner's sugar and the like starches include, but are not limited to, maize starch, potato starch, rice starch, wheat starch, pregelatinized starch, and others. Different celluloses that can be used include crystalline celluloses, such as microcrystalline cellulose, and powdered celluloses. The binders according to the present application include, but are not limited to, hydroxypropyl celluloses in different grades, hydroxypropyl methylcelluloses in different grades, polyvinylpyrrolidone in different grades, copovidones, powdered acacia, gelatin, guar gum, carbomers, methylcelluloses, polymethacrylates and starches. The different useful disintegrants include, but are not limited to carmellose calcium, carboxymethylstarch sodium, croscarmellose sodium, crospovidone (crosslinked homopolymer of N-vinyl-2-pyrrolidone) and low-substituted hydroxypropyl celluloses. Other useful disintegrants include sodium starch glycolate, colloidal silicon dioxide, alginic acid and alginates, acrylic acid derivatives and different starches.

The formulation of the present invention may consist of a dissolution enhancing agent which include but not limited to polyoxyethylene sorbitan fatty acid esters e.g. mono- and tri-lauryl, palmtyl, stearyl and oleyl esters e.g of the type known and commercially available under the trade name Tween® including the products: Tween® 20 [polyoxyethylene 20 sorbitan monolaurate], Tween® 21 [polyoxyethylene (4) sorbitan monolaurate], Tween® 40 [polyoxyethylene 20 sorbitan monopalmitate], Tween® 60 [polyoxyethylene 20 sorbitan monostearate], Tween® 61 [polyoxyethylene (4) sorbitan monostearate], Tween® 65 [polyoxyethylene 20 sorbitan tristearate], Tween® 80 [polyoxyethylene 20 sorbitan monooleate], Tween® 81 [polyoxyethylene (5) sorbitan monooleate], Tween® 85 [polyoxyethylene 20 sorbitan trioleate], Tween® 120 [polyoxyethylene 20 sorbitan monoisostearate]. Optionally, many other hydrophilic surfactants that can be used are polyoxyethylene fatty acid esters, polyoxylglycerides, polyoxyethylene-polyoxypropylene co-polymers, dioctylsuccinate, dioctyl sodium sulfosuccinate or, sodium lauryl sulfate, tocopherol-PEG succinate, phospholipids (in particular lecithin), propylene glycol mono- and di-fatty acid esters, bile salts and the like can be used as dissolution enhancing agents.

Dissolution enhancers may also consist of different complexing agents include but are not limited to cyclodextrins (α-Cyclodextrin, β-Cyclodextrin, γ-Cyclodextrin), povidone (Kollidon®, Plasdone®), polyethylene glycols, caffeine, xanthene, genistic acid and the like.

The antioxidant and moisture protectant may be present either as a part of a formulation or as a packaging component. Antioxidants can be present in amounts effective to retard decomposition of a drug that is susceptible to oxidation.

The lubricants include but not limited to magnesium stearate, glyceryl monostearates, palmitic acid, talc, carnauba wax, calcium stearate sodium, sodium or magnesium lauryl sulfate, sodium stearyl fumarate, calcium soaps, zinc stearate, polyoxyethylene monostearates, calcium silicate, silicon dioxide, hydrogenated vegetable oils and fats, stearic acid, and any combinations thereof.

The glidant materials, which improve the flow of powder blends, pellets, etc. and help to minimize dosage form weight variations, can be used. The useful glidants include, but are not limited to, silicon dioxide, talc, kaolin, and any combinations thereof.

Sweeteners that can be used include sucrose, sucralose, aspartame, mannitol, sodium saccharine, propylene glycol, acesulfame potassium, sucralose, neotame and aspartame.

The flavoring agents include pharmaceutically acceptable natural oils, natural flavors, and artificial flavors. They include without limitation thereto, menthol, peppermint, wintergreen, orange, cherry, and other fruits, vanilla, almond and other nuts and mixture thereof.

The foregoing lists of excipients and processing aids are not intended to be exhaustive, but are merely representative of members of the different categories. Those skilled in the art will be aware of many other useful substances, and their use is specifically contemplated herein. It is well-known that some of the excipients can serve more than one function in pharmaceutical formulations.

The different additives can be mixed, ground or granulated with the solid dispersion as disclosed herein to form a material suitable for the different dosage forms. The blend obtained may be slugged, suitably dry granulated using roller compactor to convert into suitable dosage forms. The preferable potentially beneficial additives include but not restricted to surface active agents (like sodium lauryl sulfate, poloxamers, polysorbate etc), drug complexing agents or, solubilizers (polyethylene glycols, caffeine, xanthene, gentisic acid, cyclodextrins etc), disintegrants (sodium starch glycolate, sodium alginate, carboxy methyl cellulose, methyl cellulose, croscarmellose sodium etc), binders (methyl cellulose, microcrystalline cellulose, starch, gums, such as guar gum, tragacanth etc), lubricants (magnesium stearate and calcium stearate), pH modifiers (acetic acid, ascorbic acid, phosphoric acid, bases such as sodium acetate, potassium acetate, calcium oxide, magnesium oxide, trisodium phosphate, sodium hydroxide, calcium hydroxide, aluminium hydroxide, buffers which generally comprises of mixtures of acids and the salts of acids).

It will be apparent to those skilled in the art that various modifications and variations can be made in the practice of the present invention without departing from the spirit and scope of the invention. It is also intended that the specification and examples to be considered as exemplary in nature and the variations that do not depart from the essence of the invention are intended to be within the scope of the invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope. The invention has been described with reference to various specific and preferred embodiments and techniques. However, it should be understood that many variations and modifications may be made while remaining within the rationale and scope of the invention.

FIG. 1 shows the comparison of bioavailability study of the formulation of the present invention with respect to NRC-AN-019 "as is". The study discloses better bioavailability characteristics of NRC-AN-019 in the formulation of the present invention than NRC-AN-019 as such. Thus, the optimum bioavailability can be achieved for the therapeutic effectiveness of NRC-AN-019. The maximum concentration and AUC of the formulation of the present invention are substantially higher than that of NRC-AN-019 "as is" due to better absorption characteristics of the solid dispersion of NRC-AN-019 in amorphous or, partially amorphous or, crystalline form. The details of the process of the invention are provided in the examples given below which is provided by way of illustration only and therefore should not be construed to limit the scope of the invention. The preparation of the present invention that can be administered by the oral route is carried out according to the following process.

EXAMPLES

The description of the particular features of the present invention pertaining to the preparation and compositions of the solid dispersions comprising NRC-AN-019 which is dispersed within polymer matrix in amorphous or, partially amorphous or, crystalline form is enumerated in the below mentioned examples that are characterized by their crystallinity, stability and bioavailability. The bioavailability of these solid dispersions is compared with NRC-AN-019 "as is" without the benefit of the polymer matrix. The below mentioned examples are intended to be illustrative embodiments of the invention, which are mere exemplary and are not limiting or, restrictive to the scope of the invention. A person skilled in the art may make variations and modifications without deviatory from the spirit of scope of invention. All such modifications and variations are intended to be included within the scope of the invention.

Example 1 to 13

The solid dispersions of amorphous or, partially amorphous or, crystalline form NRC-AN-019 in mono polymer system were prepared comprising the ingredients shown in Table 1 (values for content are given as parts of the total dispersion) which comprise of NRC-AN-019 and cellulosic polymers in the respective polymer system.

TABLE 1

| Dispersions/ Examples | Drug NRC-AN-019 | Cellulosic Polymers | | | | |
|---|---|---|---|---|---|---|
| | | HPMCP HP-55 | HPMCAS | Cellulose Acetate Phthalate | Cellulose Acetate | Ethyl Cellulose |
| 1 | 1 | 0 | 4 | 0 | 0 | 0 |
| 2 | 1 | 2 | 0 | 0 | 0 | 0 |
| 3 | 1 | 4 | 0 | 0 | 0 | 0 |
| 4 | 1 | 0 | 0 | 4 | 0 | 0 |
| 5 | 1 | 0 | 0 | 0 | 0 | 2 |
| 6 | 1 | 0 | 0 | 0 | 4 | 0 |

Compositions of example 1 to 6 were prepared by dissolving NRC-AN-019 and the mono polymer system (as parts of the total dispersion) in DMA to form solvent phase. The resultant homogenous solution was then added to aqueous acid phase (0.01 N HCl) under stirring. This addition resulted in the precipitation of NRC-AN-019 in the polymer system in subdivided state. The ratio of solid mass (NRC-AN-019 and polymer system) to DMA was in the range of 1:3 to 1:6, whereas the ratio of DMA to aqueous acid phase varied in the range from 1:5 to 1:12. Thus, formed co-precipitate was then washed with aqueous acid phase, i.e., 0.01 N HCl and 0.001N HCl to remove DMA. The wet mass was filtered, dried, milled and sieved to achieve uniform particle size distribution.

The solid dispersions of amorphous or, partially amorphous or, crystalline form of NRC-AN-019 in mono polymer system were prepared comprising the ingredients shown in Table 2 (values for content are given as parts of the total dispersion) which comprise of NRC-AN-019 and polymethacrylate polymers in the respective polymer system.

TABLE 2

| | | Dispersions | | | |
|---|---|---|---|---|---|
| Examples | Drug NRC-AN-019 | Polymethacrylate Polymers | | | |
| | | Eudragit® L 100 55 | Eudragit® L 100 | Eudragit® S 100 | Eudragit® EPO |
| 7 | 1 | 3 | 0 | 0 | 0 |
| 8 | 1 | 4 | 0 | 0 | 0 |
| 9 | 1 | 6 | 0 | 0 | 0 |
| 10 | 1 | 0 | 0 | 8 | 0 |
| 11 | 1 | 0 | 4 | 0 | 0 |

TABLE 2-continued

| | | Dispersions | | | |
|---|---|---|---|---|---|
| | Drug NRC- | Polymethacrylate Polymers | | | |
| Examples | AN-019 | Eudragit® L 100 55 | Eudragit® L 100 | Eudragit® S 100 | Eudragit® EPO |
| 12 | 1 | 0 | 0 | 0 | 2 |
| 13 | 1 | 0 | 0 | 0 | 4 |

Compositions of example 7 to 13 were prepared in analogous manner to that of example 1 to 6 except mono polymer system containing cellulosic polymers was replaced with polymethacrylate polymers (as parts of the total dispersion).

Example 14 to 45

The solid dispersions of amorphous or, partially amorphous or, crystalline form NRC-AN-019 in binary polymer system were prepared comprising the ingredients shown in Table 3 and 4 (values for content are given as parts of the total dispersion) which comprise of NRC-AN-019 and different range of polymers in the respective polymer system.

TABLE 3

| | Dispersions | | | |
|---|---|---|---|---|
| | Drug NRC- | Polymethacrylate Polymers | | Cellulosic |
| Examples | AN-019 | Eudragit® L 100 55 | Eudragit® S 100 | Polymer HPMCAS |
| 14 | 1 | 2 | 4 | 0 |
| 15 | 1 | 2.5 | 2.5 | 0 |
| 16 | 1 | 3 | 3 | 0 |

TABLE 3-continued

| | Dispersions | | | |
|---|---|---|---|---|
| | Drug NRC- | Polymethacrylate Polymers | | Cellulosic |
| Examples | AN-019 | Eudragit® L 100 55 | Eudragit® S 100 | Polymer HPMCAS |
| 17 | 1 | 3.5 | 1.5 | 0 |
| 18 | 1 | 3.5 | 3.5 | 0 |
| 19 | 1 | 4 | 2 | 0 |
| 20 | 1 | 4.5 | 2.5 | 0 |
| 21 | 1 | 3 | 1 | 0 |
| 22 | 1 | 1.5 | 3.5 | 0 |
| 23 | 1 | 3.5 | 0 | 3.5 |
| 24 | 1 | 2.5 | 0 | 4.5 |

TABLE 4

| | Drug | Polymethacrylate | Cellulosic Polymers | | | |
|---|---|---|---|---|---|---|
| Dispersions/Examples | NRC-AN-019 | Polymer Eudragit® L 100 55 | HPMCAS | HPMCP HP-55 | Cellulose Acetate Phthalate | Ethyl Cellulose |
| 25 | 1 | 2.5 | 0 | 0 | 4.5 | 0 |
| 26 | 1 | 3 | 0 | 0 | 3 | 0 |
| 27 | 1 | 3.5 | 0 | 0 | 1.5 | 0 |
| 28 | 1 | 4.5 | 0 | 0 | 2.5 | 0 |
| 29 | 1 | 4 | 0 | 0 | 2 | 0 |
| 30 | 1 | 5 | 0 | 0 | 2 | 0 |
| 31 | 1 | 4 | 0 | 0 | 0 | 1 |
| 32 | 1 | 5 | 0 | 0 | 0 | 1 |
| 33 | 1 | 0 | 4 | 0 | 2 | 0 |
| 34 | 1 | 2 | 0 | 2 | 0 | 0 |
| 35 | 1 | 2 | 0 | 3 | 0 | 0 |
| 36 | 1 | 2.5 | 0 | 4.5 | 0 | 0 |
| 37 | 1 | 3 | 0 | 1 | 0 | 0 |
| 38 | 1 | 3.5 | 0 | 3.5 | 0 | 0 |
| 39 | 1 | 4 | 0 | 1 | 0 | 0 |
| 40 | 1 | 4.5 | 0 | 2.5 | 0 | 0 |
| 41 | 1 | 5 | 0 | 1 | 0 | 0 |
| 42 | 1 | 6 | 0 | 2 | 0 | 0 |
| 43 | 1 | 0 | 0 | 6 | 0 | 1 |
| 44 | 1 | 0 | 0 | 6 | 0 | 1.5 |
| 45 | 1 | 0 | 0 | 6 | 0 | 2 |

Compositions of example 14 to 45 were prepared in analogous manner to that of example 1 to 13 except mono polymer system was replaced with binary polymer system (as parts of the total dispersion).

Example 46 to 55

The solid dispersions of amorphous or, partially amorphous or, crystalline form NRC-AN-019 in tertiary polymer system were prepared comprising the ingredients shown in Table 5 and 6 (values for content are given as parts of the total dispersion) which comprise of NRC-AN-019 and different range of polymers in the respective polymer system.

TABLE 5

| Dispersions/Examples | Drug NRC-AN-019 | Polymethacrylate Polymers | | Cellulosic Polymers | | | |
|---|---|---|---|---|---|---|---|
| | | Eudragit® L 100 55 | Eudragit® S 100 | HPMCP HP-55 | HPMCAS | Cellulose Acetate Phthalate | Ethyl Cellulose |
| 46 | 1 | 3 | 0 | 3 | 0 | 0 | 1 |
| 47 | 1 | 3 | 0 | 3 | 0 | 0 | 2 |
| 48 | 1 | 5 | 0 | 1 | 0 | 0 | 1.5 |
| 49 | 1 | 5 | 1 | 1 | 0 | 0 | 0 |
| 50 | 1 | 5 | 1 | 0 | 1 | 0 | 0 |
| 51 | 1 | 4 | 2 | 0 | 0 | 2 | 0 |

Compositions of example 46 to 51 were prepared in analogous manner to that of example 1 to 13 except mono polymer system was replaced with tertiary polymer system (as parts of the total dispersion) and in compositions of example 52 to 55, additionally Carbopol® (commonly referred as polyacrylic acid) was added to the solvent phase in the form of a dispersion in water.

TABLE 6

| | Dispersions | | | | |
|---|---|---|---|---|---|
| | Drug NRC-AN-019 | Polymethacrylate Polymers | | Cellulosic | Polyacrylic acid |
| Examples | | Eudragit® L 100 55 | Eudragit® S 100 | Polymer HPMCAS | Carbopol® 974 |
| 52 | 1 | 2.5 | 0 | 4.5 | 0.05 |
| 53 | 1 | 2 | 1 | 0 | 0.05 |
| 54 | 1 | 2 | 1 | 0 | 0.1 |
| 55 | 1 | 4 | 2 | 0 | 0.08 |

Example 56 to 61

The solid dispersions of amorphous or, partially amorphous or, crystalline form of NRC-AN-019 in quaternary polymer system were prepared comprising the ingredients shown in Table 7 and 8 (values for content are given as parts of the total dispersion) which comprise of NRC-AN-019 and different range of polymers in the respective polymer system.

TABLE 7

| Dispersions/Examples | Drug NRC-AN-019 | Polymethacrylate Polymers | | Cellulosic Polymers | | |
|---|---|---|---|---|---|---|
| | | Eudragit® L 100 55 | Eudragit® S 100 | HPMCP HP-55 | Cellulose Acetate Phthalate | Ethyl Cellulose |
| 56 | 1 | 2 | 1 | 4 | 0 | 0.5 |
| 57 | 1 | 2 | 1 | 0 | 4 | 0.5 |
| 58 | 1 | 5 | 1 | 1 | 0 | 0.5 |

TABLE 8

| Dispersions/Examples | Drug NRC-AN-019 | Polymethacrylate Polymers | | Polyacrylic acid | Cellulosic Polymers | |
|---|---|---|---|---|---|---|
| | | Eudragit® L 100 55 | Eudragit® S 100 | Carbopol® 974 | HPMCAS | Ethyl Cellulose |
| 59 | 1 | 2 | 1 | 0.10 | 0 | 0.5 |
| 60 | 1 | 2 | 1 | 0 | 4 | 0.5 |
| 61 | 1 | 5 | 1 | 0 | 1 | 0.5 |

Compositions of example 56 to 61 were prepared in analogous manner to that of example 1 to 13 except that mono polymer system was replaced with quaternary polymer system (as parts of the total dispersion) and in composition of example 59, additionally Carbopol® (commonly referred as polyacrylic acid) was added to the solvent phase in the form of a dispersion in water.

Example 62 to 68

TABLE 9

| Dispersions/ Examples | Drug NRC-AN-019 | Polymethacrylate Polymer Eudragit® L 100 55 | Cellulosic Polymer HPMCP HP-55 | Lipid Glyceryl behenate | Lipid Imwitor® 491 | Surfactant Tocopherol PEG Succinate |
|---|---|---|---|---|---|---|
| 62 | 1 | 0 | 6 | 2 | 0 | 0 |
| 63 | 1 | 0 | 6 | 1 | 0 | 0 |
| 64 | 1 | 0 | 6 | 1.5 | 0 | 0 |
| 65 | 1 | 3 | 3 | 1 | 0 | 0 |
| 66 | 1 | 3 | 3 | 2 | 0 | 0 |
| 67 | 1 | 5 | 1 | 1.5 | 0 | 0 |
| 68 | 1 | 0 | 5 | 0 | 2 | 1 |

Compositions of example 62 to 68 were prepared in analogous manner to that of example 1 to 13, except that with the addition of a lipid and surfactant. The solid dispersions of amorphous or, partially amorphous or, crystalline form NRC-AN-019 in mono and binary polymer system were prepared with the composition as shown in Table 9 (values for content are given as parts of the total dispersion) which comprise of NRC-AN-019 and different range of polymers with the inclusion of lipids like glyceryl behenate and Imwitor 491® (commonly referred as glycerol monostearate). The composition of example 68 contains a hydrophilic surfactant (Tocopherol PEG Succinate) in addition to Imwitor® 491.

Compositions of Example 62 to 67 were prepared by dissolving NRC-AN-019 and respective polymer in DMA to get a clear solution. Glyceryl behenate was added to the solution under stirring by the application of heat to 70° C. to get homogenous single phase solution. The resultant solution under stirring and application of heat to 70° C. was then added to aqueous acid phase (0.01 N HCl) to avoid solidification of glyceryl behenate at room temperature. This step involves high shear mixing of the aqueous acid phase (0.01 N HCl) resulting in the co-precipitation of NRC-AN-019 in the polymer and lipid system matrix in subdivided state. Glyceryl behenate was replaced with Imwitor® 491 in composition of example 68 without the application of heat. Additionally, tocopherol PEG succinate was added in composition of example 68.

Example 69 to 74

TABLE 10

| Dispersions/ Examples | Drug NRC-AN-019 | Polymethacrylate Polymers Eudragit® L 100 55 | Polymethacrylate Polymers Eudragit® S 100 | Cellulosic Polymer HPMCP HP-55 | Polyacrylic acid Carbopol® 974 | Acid Fumaric acid | Surfactant Poloxamer® 188 |
|---|---|---|---|---|---|---|---|
| 69 | 1 | 4 | 0 | 1 | 0 | 0 | 1 |
| 70 | 1 | 2 | 1 | 0 | 0.05 | 0 | 0.5 |
| 71 | 1 | 2 | 1 | 0 | 0.05 | 1 | 0.5 |
| 72 | 1 | 2 | 1 | 0 | 0.1 | 0.5 | 0.0 |
| 73 | 1 | 2 | 1 | 1 | 0.05 | 1 | 0.5 |
| 74 | 1 | 4 | 2 | 1 | 0.1 | 0.5 | 0.5 |

Compositions of example 69 to 74 were prepared in analogous manner to that of example 1 to 13 except that mono polymer system was replaced with multi polymer system (binary, tertiary and quaternary). The composition comprising of the ingredients as enumerated in Table 10 (values for content are given as parts of the total dispersion) which contains NRC-AN-019 and different range of polymers, Poloxamer® 188 and fumaric acid in the system. Compositions were prepared by dissolving NRC-AN-019 along with respective polymers, fumaric acid and Poloxamer® 188 in DMA. Carbopol® was added to the solvent phase in the form of dispersion in water. The resultant homogenous solution was then added to aqueous acid phase (0.01 N HCl) containing 0.1% w/v of Poloxamer® 188 under stirring.

Example 75 to 80

TABLE 11

| | | Dispersions | | | |
|---|---|---|---|---|---|
| Examples | Drug NRC-AN-019 | Polymethacrylate Polymer Eudragit® L 100 55 | Polyacrylic acid Carbopol® 974 | Water soluble polymers Copovidone® | Water soluble polymers Polyvinyl pyrrolidone |
| 75 | 1 | 2 | 0.05 | 0 | 0.5 |
| 76 | 1 | 2 | 0.05 | 0.5 | 0 |

Compositions of example 75 and 76 were prepared in analogous manner to that of example 1 to 13. In composition of example 75, polyvinylpyrrolidone was added to the solvent phase as hydrophilic polymer. Carbopol® was added to the solvent phase in the form of dispersion in water. The resultant homogenous solution was then added to aqueous acid phase (0.01 N HCl) containing 0.1% w/v of polyvinylpyrrolidone under stirring. Polyvinylpyrrolidone was replaced with copovidone in example 76.

TABLE 12

| Dispersions/Examples | Drug NRC-AN-019 | Polymethacrylate Polymers | | Cellulosic Polymer HPMCP HP-55 | Polyacrylic acid Carbopol® 974 | Acid Fumaric acid | Water soluble polymers | |
|---|---|---|---|---|---|---|---|---|
| | | Eudragit® L 100 | Eudragit® S 100 | | | | HPβCD | Soluplus® |
| 77 | 1 | 4 | 2 | 1 | 0.1 | 0.5 | 0.5 | 0 |
| 78 | 1 | 2 | 1 | 1 | 0.05 | 1 | 0 | 0.5 |

Compositions of example 77 and 78 as shown in Table 12, were prepared in analogous manner to that of example 71. In composition of example 77, hydroxypropyl-β-cyclodextrin (HPβCD) was added to the solvent phase as hydrophilic polymer. The resultant homogenous solution was then added to aqueous acid phase (0.01 N HCl) containing 0.1% w/v of HPβCD under stirring. HP-β-CD was replaced with Soluplus® in example 78 and it was added to aqueous acid phase (0.01 N HCl) containing 0.1% w/v of Soluplus® under stirring.

TABLE 13

| Dispersions/Examples | Drug NRC-AN-019 | Polymethacrylate Polymers | | Cellulosic Polymer HPMCP HP-55 | Polyacrylic acid Carbopol® 974 | Acid Fumaric acid | Water soluble Polymers | |
|---|---|---|---|---|---|---|---|---|
| | | Eudragit® L 100 55 | Eudragit® S 100 | | | | Copovidone | Hydroxypropyl Cellulose |
| 79 | 1 | 4 | 2 | 1 | 0.1 | 0.5 | 0 | 0.5 |
| 80 | 1 | 4 | 2 | 1 | 0.1 | 0.5 | 0.1 | 0 |

Compositions of example 79 and 80 as enumerated in Table 13, were prepared in analogous manner to that of example 77. In composition of example 79, hydroxypropyl cellulose was added to the solvent phase. The resultant homogenous solution was then added to aqueous acid phase (0.01 N HCl) under stirring. Hydroxypropyl cellulose was replaced with copovidone in example 80.

Example 81 to 88

The components illustrated by the examples 81 to 88 are expressed in parts by weight based on each composition.

Compositions of example 81 to 88 as enumerated in Table 14, were prepared in analogous manner to that of example 1 to 13 except mono polymer system was replaced with multi polymer system (as parts of the total dispersion).

Example 89

This example illustrates the general method of preparation of the solid polymer complexes of NRC-AN-019 in the mixture of different polymers.

Step 1: Preparation of the Solvent Phase

NRC-AN-019 and the polymer system in the respective ratio were dissolved in dimethylacetamide at room temperature under stirring which resulted in a homogenous solution.

Step 2: Preparation of the Aqueous Acid Phase

Aqueous acid phase, 0.01 N HCl was prepared at room temperature as antisolvent and solvent for washing.

Step 3: Co-Precipitation

High Shear Homogenization:

The tip speed of the rotor in the high shear homogenizer was introduced into the aqueous phase.

TABLE 14

| Ingredients | Example 81 | Example 82 | Example 83 | Example 84 | Example 85 | Example 86 | Example 87 | Example 88 |
|---|---|---|---|---|---|---|---|---|
| NRC-AN-019 | 1 | 1 | 1 | 1 | 1 | 1 | 1 | 1 |
| Eudragit® L100 55 | 6 | 5 | 5 | 5 | 5 | 5 | 1 | 3 |
| CAP | 2 | 0 | 0 | 0 | 0 | 0 | 0 | 0 |
| Eudragit® S 100 | 0 | 1 | 0 | 1 | 0 | 1 | 1 | 0.75 |
| HPMCAS | 0 | 1 | 0 | 0 | 0 | 0 | 0 | 0 |
| HPMCP HP 55 | 0 | 0 | 1 | 1 | 1 | 1 | 5 | 0 |
| Ethylcellulose | 0 | 0.5 | 0 | 0 | 1.5 | 0.5 | 0 | 0.75 |

Solvent Phase Dosing:

The drug polymer solution prepared in step 1 was dosed with a peristaltic pump and an injector nozzle pointing towards the aqueous phase with the simultaneous high shear homogenization to form precipitate mass.

Step 4: Isolation and Washing

The subsequent step to the co-precipitation is dispersing of the precipitates under the homogenization for an additional time. The obtained suspension was separated using suction filter. The isolated solid dispersions was washed with 0.01 N HCl followed 0.001 N HCl in order to remove the DMA. The wet mass was dried and sieved to achieve uniform particle size distribution.

The variances with respect to the compositions and procedure described herein are embodied as exemplary but not intended as limitations on the scopes of the invention.

Example 90

In-Situ Salt Formation

NRC-AN-019 chemically known as, (3,5-Bis trifluoromethyl)-N-[4-methyl-3-(4-pyridin-3yl-pyrimidin-2-yl-amino) phenyl]benzamide having functionalities of weakly basic centers which form organic salt complexes with different acids such as benzene sulfonic acid, P-toluene sulfonic acid, sulfosuccinic acid, methane sulfonic acid and lauryl sulfosuccinic acid along with the respective polymer in situ during the processing. The selection of the organic acid and the polymers is apparent to those skilled in the art. Such salts provide advantage over the free base such as improved solubility, lower melting point and enhanced oral absorption. In situ salt formation may be attempted by the process of spray drying, pH controlled precipitation, solvent controlled precipitation or, solvent evaporation. The resulting solid may be amorphous or, partially amorphous or, crystalline form.

Example 91

Compositions from the above examples were prepared in analogous manner to that of example 1 to 13 except that the antisolvent phase taken for spraying the solvent phase is selected from different solvents which are not intended to be exhaustive but are merely representative. The list includes methylene chloride, toluene, acetonitrile, ethyl acetate, water or a mixture thereof. Compositions were prepared by dissolving NRC-AN-019 along with respective polymers and the hydrophilic excipient in dimethylacetamide. The resultant homogenous solution was then added to the antisolvent phase.

Example 92

Figure 2:
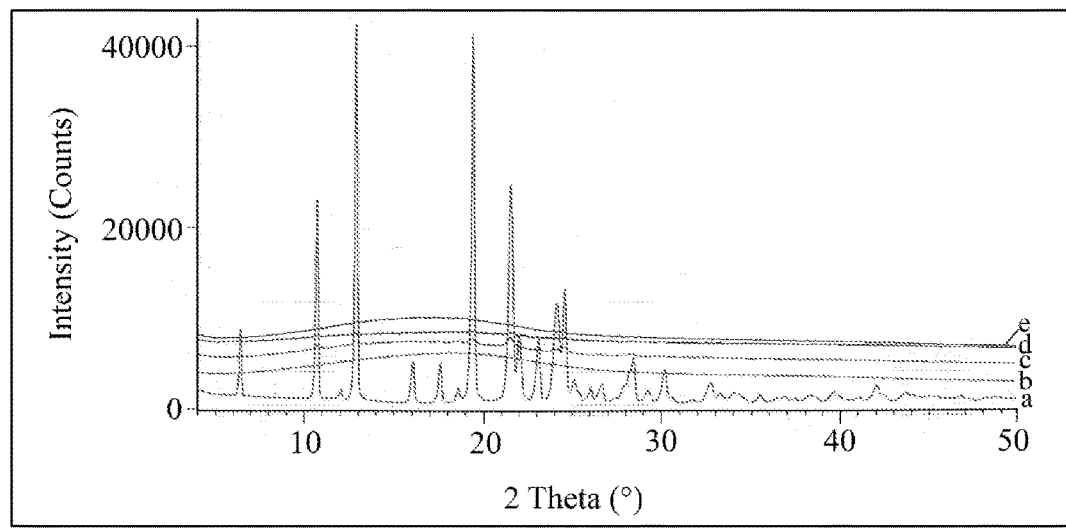
FIG. 2 is a comparison of powder X-ray diffraction pattern of NRC-AN-019 "as is" (a) and solid dispersions of example 81 (b), example 82 (c), example 83 (d) and example 84 (e).
Figure 3:
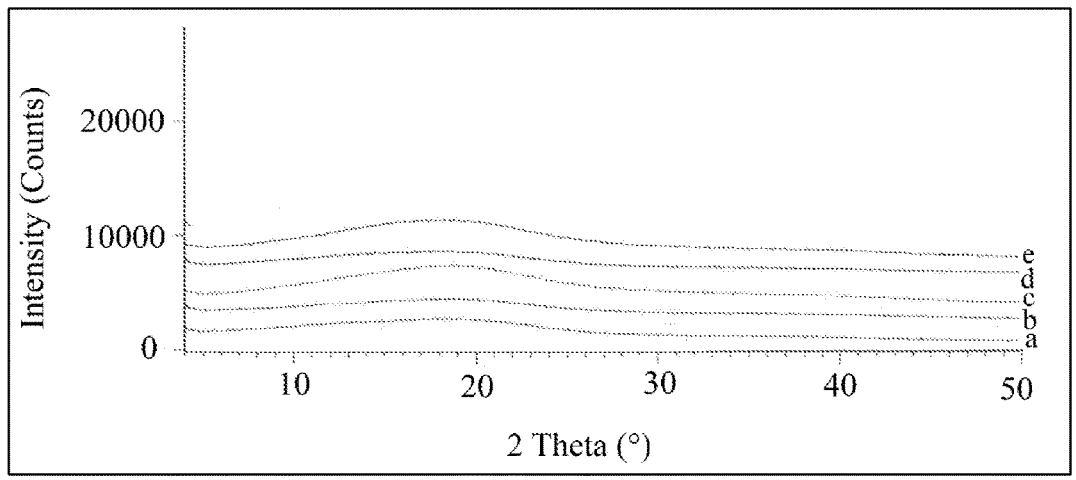
FIG. 3 illustrates the stability of the solid dispersion corresponding to example 81 in X-ray powder diffraction graph at Initial (a); 1 month at 25° C. 60% RH (b); 3 months at 25° C. 60% RH (c); 1 month at 40° C. 75% RH (d); and 3 months at 40° C. 75% RH (e).
Figure 4:
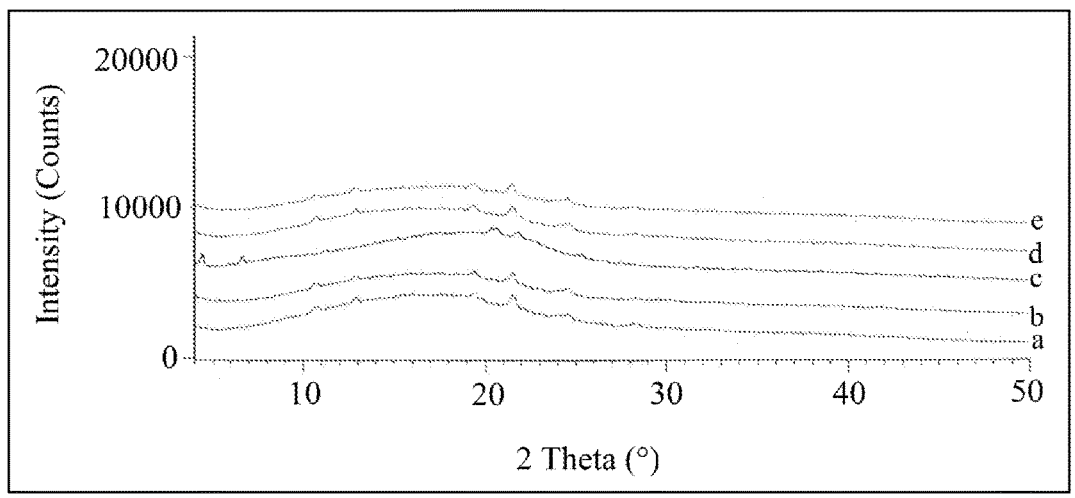
FIG. 4 illustrates the stability of the solid dispersion corresponding to example 82 in X-ray powder diffraction graph at Initial (a); 3 months at 25° C. 60% (b); 1 month at 40° C. 75% RH (c); 2 months at 40° C. 75% RH (d); 3 months at 40° C. 75% RH (e).
Figure 5:
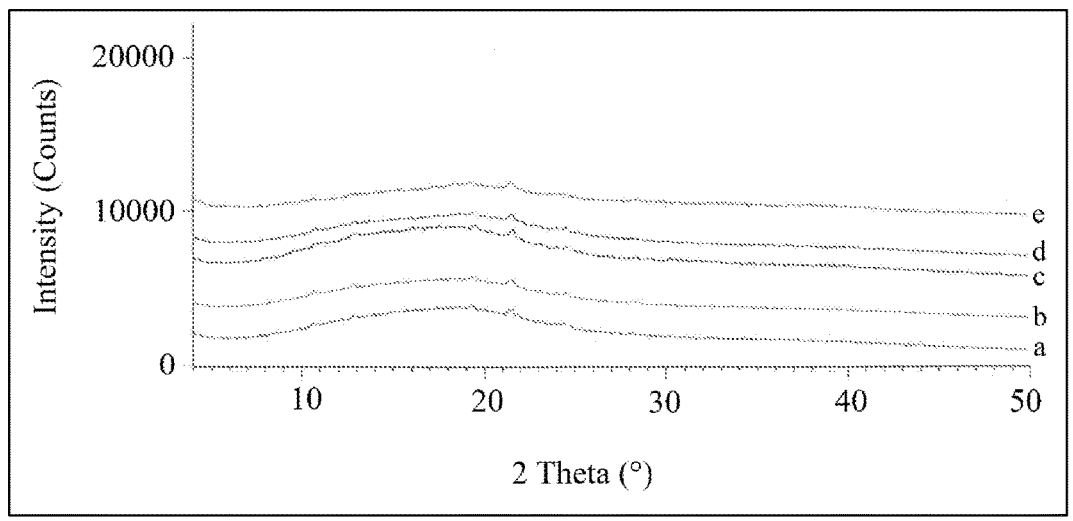
FIG. 5 illustrates the stability of the solid dispersion corresponding to example 83 in X-ray powder diffraction graph at Initial (a); 3 months at 25° C. 60% RH (b); 6 months at 25° C. 60% RH (c); 3 months at 40° C. 75% RH (d) and 6 months at 40° C. 75% RH (e).
Figure 6:
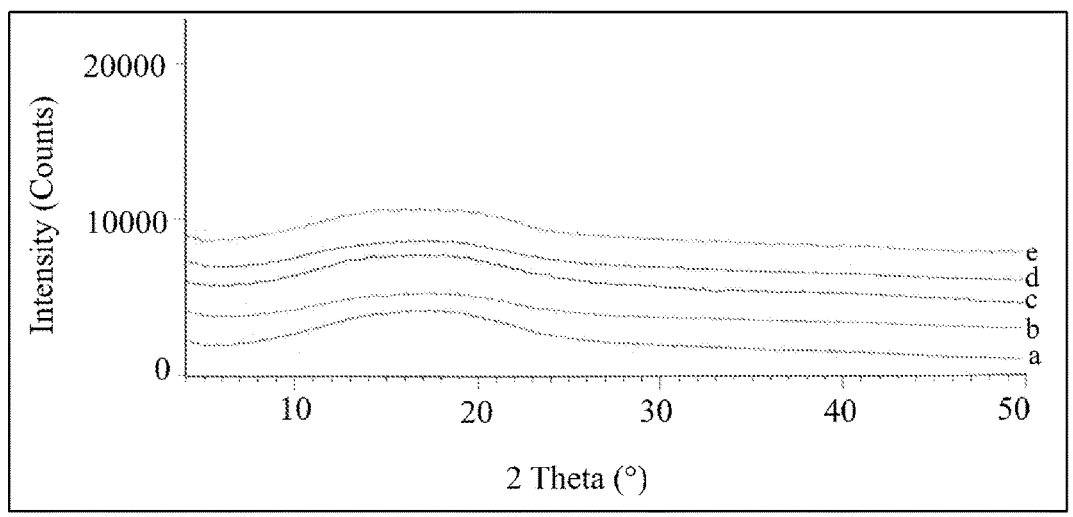
FIG. 6 illustrates the stability of the solid dispersion corresponding to example 84 in X-ray powder diffraction graph at Initial (a); 3 months at 25° C. 60% RH (b), 6 months at 25° C. 60% RH (c); 3 months at 40° C. 75% RH (d); and 6 months at 40° C. 75% RH (e).

The powder X-ray diffractogram pattern for NRC-AN-019 "as is" and as solid molecular complex as listed in Example 81 to 84 after co-precipitation in accordance with the invention is described by FIG. 2. The presence of new solid crystalline phase in case of the complexes has been revealed by appearance of new peak and alluding for the difference from diffraction pattern of NRC-AN-019 "as is". The changes in the peaks were in terms of appearance, disappearance or, decrease in the height. The complete dispersion of drug and polymers reduces the number of crystalline structures or, appearance of halo at the baseline indicating amorphous or, partially amorphous or, crystalline form of the drug in the given sample. The diffractograms were found to be more diffuse compared to the drug "as is" without characteristic peaks indicating the formation of amorphous or, partially amorphous or, crystalline form solid state. Thus, the final product sample (drug polymer complexes as co-precipitated mass) demonstrated fewer and diffuse peaks. The diffractograms of all prepared systems (drug polymer complexes) showed peaks similar to polymers and absence of major diffraction peaks corresponding to NRC-AN-019.

Example 93

The powder X-ray diffractogram pattern represented in FIGS. 3 to 6 for NRC-AN-019 and polymer complexes of example 81 to 84 exposed to long term and accelerated study conditions at 25° C.±2° C./60%±5% RH and 40° C.±2° C./75%±5% RH were compared to initial sample. It was observed that complexes did not show any additional crystalline peaks and no change from existing peaks during different stability study time points.

Example 94

It is also illustrated from the embodiment that physical mixing of NRC-AN-019 with the corresponding polymers do not affect the crystalline nature of NRC-AN-019. The height of crystalline peaks decreased due to the dilution of the drug with the excipients, however the peaks remain at the same position. The complete dispersion of drug and polymers reduces the number of crystalline peaks resembling the amorphous or, partially amorphous or, crystalline nature of the drug in the complexes. The final product demonstrated fewer and diffuse peaks. The diffractograms of different prepared systems showed peaks similar to polymers and absence of major diffraction peaks corresponding to NRC-AN-019.

Example 95

NRC-AN-019 is immobilized within the polymer matrix to form a homogenous amorphous or, partially amorphous or, crystalline form solid dispersion. The higher glass transition temperature of the polymers results in the immobilization of NRC-AN-019. The drug polymer interaction is postulated to occur by hydrogen bonding which is taking place in DMA. The physical mixture of the NRC-AN-019 and polymers exhibited different glass transition temperatures because of the separate phases. The amorphous or, partially amorphous or, crystalline form of NRC-AN-019 polymer complexes exhibit single glass transition temperature. The homogeneity of amorphous or, partially amorphous or, crystalline form NRC-AN-019 polymer complex is confirmed by the diffractogram and the thermograms.

Example 96

NRC-AN-019 solid dispersions from any of the enumerated examples can be mixed with immediate mix granulate (avicel PH 101, hydroxypropyl cellulose, sodium starch glycolate, colloidal silicon dioxide, sodium lauryl sulphate, sodium stearyl fumarate) and tablets can be prepared by compression of the resulting mixture.

Example 97

NRC-AN-019 solid dispersions from any of the enumerated examples can be suitably mixed with different pharmaceutically acceptable excipients to be finally filled into capsules and/or can be available in sachets to be readily dispersed in fluid for direct administration. The pharmaceutical composition with regard to powder for suspension mentioned in example 97 as shown in Table 15, is prepared by the procedure as follows.

Mixing: NRC-AN-019 solid dispersions was passed through a 180 micrometer aperture screen. The other constituents were suitably sieved through the same aperture screen and mixed with NRC-AN-019 solid dispersions. The blend was charged into a suitable blender and mixed for 10 minutes until uniform.

Packaging: The product was filled into suitable sachets of approximately 3.25 in×4 in, polyethylene-lined. Theoretical fill weight was found to be 12 grams in each sachet. To reconstitute, the contents were added to 50 mL purified water and stirred well.

TABLE 15

| | % w/w |
|---|---|
| Part A Ingredients | |
| NRC-AN-019 solid dispersions | 33.20 |
| Citric acid anhydrous | 0.75 |
| Tri sodium citrate | 0.50 |
| Sodium lauryl sulfate | 0.38 |
| Sodium chloride | 1.50 |
| Crospovidone | 1.25 |
| Hypromellose | 1.25 |
| Xanthan gum | 1.50 |
| Sucralose | 0.50 |
| Aspartame | 0.50 |
| Sodium benzoate | 0.05 |
| Titanium dioxide | 1.00 |
| Maltodextrin | 54.80 |
| Colloidal silicon dioxide | 1.25 |
| Menthol | 0.08 |
| Lemon flavor | 1.50 |
| Part B Ingredients | |
| Purified Water | Reconstitution: The contents were added to purified water and stirred well which resulted in a total volume of approximately 50 mL with NRC-AN-019 concentration of about 50 mg/7.5 mL |

Examples 98 to 105

The pharmaceutical compositions of example 98 to 105 (Table 16 and 17) in accordance with the present invention were prepared by blending the respective solid dispersions of NRC-AN-019 with prior sieved microcrystalline cellulose, sodium starch glycolate, hydroxypropyl cellulose (except example 98) and colloidal silicon dioxide. The blends obtained were slugged, milled and sieved to obtain uniform particle size distribution and further blended with remaining quantity of hydroxypropyl cellulose and sodium starch glycolate. Thus obtained blends were lubricated with prior sieved sodium lauryl sulphate and sodium stearyl fumarate and tablets were compressed. To aid in keeping the tablet intact during handling, to provide more elegance and to prevent moisture pick up, a thin film coating was applied by opadry white until weight gain attained 3.0% over the tablet weight.

TABLE 16

| | Example | | | |
|---|---|---|---|---|
| Components | Example 98 % (w/w) | Example 99 % (w/w) | Example 100 % (w/w) | Example 101 % (w/w) |
| Prelubrication | | | | |
| NRC-AN-019 solid dispersions | 72.34 | 72.78 | 58.73 | 67.55 |
| Microcrystalline cellulose | 13.08 | 3.18 | 19.86 | 11.03 |
| Sodium starch glycolate | 10.83 | 8.33 | 8.33 | 8.33 |
| Colloidal silicon dioxide | 0.83 | 0.21 | 0.17 | 0.17 |
| Hydroxypropyl cellulose | 0.00 | 5.83 | 5.83 | 5.83 |
| Lubrication | | | | |
| Sodium starch glycolate | 0.00 | 4.17 | 4.17 | 4.17 |
| Hydroxypropyl cellulose | 0.00 | 2.58 | 0.00 | 0.00 |
| Sodium lauryl sulphate | 2.50 | 2.50 | 2.50 | 2.50 |
| Sodium stearyl fumarate | 0.42 | 0.42 | 0.42 | 0.42 |

TABLE 17

| | Example | | | |
|---|---|---|---|---|
| Components | Example 102 % (w/w) | Example 103 % (w/w) | Example 104 % (w/w) | Example 105 % (w/w) |
| Prelubrication | | | | |
| NRC-AN-019 solid dispersions | 71.96 | 70.86 | 67.75 | 59.20 |
| Microcrystalline cellulose | 4.00 | 5.10 | 10.63 | 13.49 |
| Sodium starch glycolate | 8.33 | 8.33 | 8.33 | 9.47 |
| Colloidal silicon dioxide | 0.21 | 0.21 | 0.17 | 0.21 |
| Hydroxypropyl cellulose | 5.83 | 5.83 | 5.83 | 7.37 |
| Sodium stearyl fumarate | 0.00 | 0.00 | 0.21 | 0.26 |
| Lubrication | | | | |
| Sodium starch glycolate | 4.17 | 4.17 | 4.17 | 4.21 |
| Hydroxypropyl cellulose | 2.58 | 2.58 | 0.00 | 2.11 |
| Sodium lauryl sulphate | 2.50 | 2.50 | 2.5 | 3.16 |
| Sodium stearyl fumarate | 0.42 | 0.42 | 0.42 | 0.53 |

Examples 106 to 107

The pharmaceutical compositions of example 106 and 107 as shown in Table 18 in accordance with the present invention were prepared by analogous manner to that of example 101, microcrystalline cellulose was replaced with SmartEx® QD-100 (a coprocessed diluent comprising of mannitol, low-substituted hydroxypropyl cellulose and polyvinyl alcohol) in example 106 and with dibasic calcium phosphate:mannitol (7.5:92.5) in example 107.

TABLE 18

| Components | Examples | |
|---|---|---|
| | Example 106 % (w/w) | Example 107 % (w/w) |
| Blending | | |
| NRC-AN-019 solid dispersions | 67.75 | 67.75 |
| SmartEx ® QD-100 | 16.46 | 0.00 |
| Dibasic calcium phosphate | 0.00 | 0.80 |
| Hydroxypropyl cellulose | 0.00 | 5.83 |
| Mannitol | 0.00 | 9.83 |
| Sodium starch glycolate | 7.50 | 7.50 |
| Colloidal silicon dioxide | 0.17 | 0.17 |
| Sodium stearyl fumarate | 0.21 | 0.21 |
| Prelubrication | | |
| Sodium starch glycolate | 3.75 | 3.33 |
| Hydroxypropyl cellulose | 1.25 | 1.67 |
| Sodium lauryl sulfate | 2.50 | 2.5 |
| Lubrication | | |
| Sodium stearyl fumarate | 0.42 | 0.42 |

Example 108

Bioavailability Study in Beagle Dogs for the Compositions in Accordance with the Invention a) A multiple dose comparative bioavailability study of NRC-AN-019 in beagle dogs by oral route was studied by an open label, randomized, balanced, three-way cross over study design. NRC-AN-019 tablets corresponding to examples 100, 101 and 103 were administered by the oral route. A total of twelve healthy adult beagle dogs were divided into 3 groups consisting of four animals (2 males and 2 females) per group. All the animals were fasted overnight prior to oral administration, but were permitted water ad libitum. In three study periods for each animal, repeated dose of the assigned formulation was administered at ambient temperature. The formulations were administered orally at the dose levels of 28 mg/kg body weight. 10 mL of water was administered orally after administration of the tablets. The dogs were permitted for food and water after 2 hours of dosing.

b) A total of 26 blood samples were collected from each period and each animal from the foreleg vein in 2 mL K2 ethylenediaminetetraacetic acid vacutainers. The pre-dose blood sample of 1.0 mL (0.0 hr) was collected before dosing on day 1 from all the animals. The post-dose blood samples (1 mL each) were collected on day 1 and day 3 at 0.5, 1.0, 2.0, 3.0, 4.0, 5.0, 6.0, 7.0, 8.0, 10.0, 12.0 hours in each period. A wash out period of at least 7 days between treatments was given.

c) Blood samples were centrifuged at 3000 rpm for 10 min at 4° C. and plasma was separated, immediately transferred and stored at −20±3° C. Then, subsequent analytical procedure was followed with the use of liquid chromatography mass spectrometry technique. The areas under the blood drug concentration versus time curves are calculated by the trapezoidal rule. The analysis was done with respect to AUC (area under curve), $C_{max}$ (maximum concentration) and $T_{max}$ (time of maximum concentration).

The average AUC (ng·hr/mL) and $C_{max}$ (in ng/mL) values from typical trial runs are shown in the following table.

The data summarized in Table 19 indicate that, the tablets prepared from the NRC-AN-019 solid dispersion have shown bioavailability enhancement. The superior pharmacokinetic performance can be explained based on the solid state properties.

TABLE 19

| Example | Example 100 | Example 101 | Example 103 |
|---|---|---|---|
| $AUC_{0-\infty}$ (ng · hr/mL) | 18289.17 ± 11792.97 | 12208.38 ± 6259.13 | 11146.89 ± 5881.182 |
| $AUC_{0-t}$ (ng · hr/mL) | 14936.53 ± 8580.26 | 10734.07 ± 5382.39 | 10012.202 ± 5356.43 |
| $C_{max}$ (ng/mL) | 593.92 ± 204.21 | 485.1166 ± 218.84 | 455.483 ± 137.87 |
| $T_{max}$ (hrs) | 4.25 ± 1.912 | 3.25 ± 1.484 | 3.5 ± 1.381 |

Example 109

NRC-AN-019 active pharmaceutical ingredient (API) and the compositions of the present invention were administered through oral gavage at 40 mg/kg·bw in the form of a suspension in albino wistar rats. The average $C_{max}$ and $AUC_{0-\infty}$ of API are 33.7 ng/mL and 453 ng·hr/mL respectively. The $C_{max}$ and $AUC_{0-\infty}$ for the compositions of the present invention vary between 900 ng/mL to 2000 ng/mL and 7500 ng·hr/mL to 16000 ng·hr/mL respectively.

Example 110 to 112

The solid dispersions of NRC-AN-019 were also prepared by hot melt extrusion technology. The data summarized in Table 20 indicate composition details of solid dispersions of NRC-AN-019 in amorphous or, partially amorphous or, crystalline form prepared by hot melt extrusion technology.

TABLE 20

| Components | Example 110 % (w/w) | Example 111 % (w/w) | Example 112 % (w/w) |
|---|---|---|---|
| NRC-AN-019 | 11.11 | 10.00 | 10.00 |
| Eudragit ® L100 55 | 0.00 | 0.00 | 40.01 |
| HPMCAS | 44.45 | 40.01 | 0.00 |
| Soluplus ® | 0.00 | 10.00 | 10.00 |
| Poloxamer ® 188 | 11.11 | 10.00 | 10.00 |
| Docusate sodium | 0.56 | 0.50 | 0.50 |
| Sodium lauryl sulfate | 1.67 | 1.50 | 1.50 |
| Crospovidone | 3.33 | 3.00 | 3.00 |
| Fumaric acid | 12.89 | 11.60 | 11.60 |
| Povidone | 4.59 | 4.13 | 4.13 |
| Polyethylene glycol 1000 | 3.33 | 3.00 | 3.00 |
| Dibasic calcium phosphate | 5.56 | 5.00 | 5.00 |
| Sodium stearyl fumarate | 1.39 | 1.25 | 1.25 |

The pharmaceutical compositions of example 110 to 112 in accordance with the present invention were prepared by sifting of individual ingredients through a suitable sieve and mixing them by a high shear mixture. Example 110 involves blending of NRC-AN-019 with HPMCAS as the primary polymer followed by addition of processing aids like povidone as binder, Poloxamer® 188, sodium lauryl sulphate and docusate sodium as surfactants, crospovidone as disintegrant, PEG 1000 as the plasticizer, dibasic calcium phosphate as diluent, sodium stearyl fumarate as lubricant and fumaric acid as acidifier.

The homogenous mixtures of NRC-AN-019 and other ingredients were fed into feeder of the melt extruder at a controlled rate. The process involves the application of heat to the homogenously mixed mass to form solid dispersion. It was kneaded to the heated barrel that consists of extruder screws to convey and mix the fed materials, and an exit port, which consists of an optional die to shape the extruding mass. As the physical mixture is conveyed through heated screws, it is transformed into its "fluid-like state," which allows intimate and homogeneous mixing by the high shear of extruder screws. The intimately mixed hot mass, that is, solid dispersion, is extruded through the die opening. The extruded strands were subjected for sudden cooling and precisely cut and sized into powders.

The pharmaceutical compositions of example 111 and 112 in accordance with the present invention were prepared by analogous manner to that of example 110, HPMCAS was additionally added with Soluplus® in example 111 and HPMCAS was replaced with Eudragit® L 100 55 and Soluplus® in example 112 as the primary polymer(s).

Example 113 to 115

The solid dispersions of NRC-AN-019 were also prepared by solvent evaporation method. The pharmaceutical compositions of example 113 to 115 as shown in Table 21 in accordance with the present invention were prepared by dissolving NRC-AN-019 and the polymers in 1:1 (w/w) mixture of acetone:ethanol. Additionally, suitable amount (molar ratio) of concentrated HCl was added to form in-situ hydrochloride salt of NRC-AN-019. In context to the polymer system, composition corresponding to example 113 contains Eudragit® L100 55 and HPMCP HP-55, example 114 contains Eudragit® L100 55, Eudragit® S100, HPMCAS and ethyl cellulose whereas, example 115 contains Eudragit® L100 55, ethyl cellulose and povidone.

The mixtures were visually inspected to confirm that NRC-AN-019 and the polymers were fully dissolved and one-phase solutions were formed. After confirmation of clear one phase solution, these were subjected for suitable addition of processing aids like magnesium stearate, colloidal silicon dioxide and microcrystalline cellulose. Poloxamer® 188 was added as surfactant to every composition.

TABLE 21

| Components | Example 113 % (w/w) | Example 114 % (w/w) | Example 115 % (w/w) |
|---|---|---|---|
| NRC-AN-019 | 13.97 | 10.05 | 11.17 |
| Eudragit ® L100 55 | 69.83 | 50.25 | 55.87 |
| Eudragit ® S 100 | 0.00 | 10.05 | 0.00 |
| HPMCAS | 0.00 | 10.05 | 0.00 |
| HPMCP HP-55 | 13.97 | 0.00 | 0.00 |
| Ethyl cellulose | 0.00 | 5.03 | 5.59 |
| Povidone | 0.00 | 0.00 | 11.17 |
| Magnesium stearate | 0.82 | 1.01 | 1.12 |
| Colloidal silicon dioxide | 0.00 | 2.51 | 2.79 |
| Microcrystalline cellulose | 0.00 | 10.05 | 11.17 |
| Poloxamer ® 188 | 1.40 | 1.01 | 1.12 |

This solution was mixed to obtain a light yellow color suspension and the solvent is evaporated using rotavapor the centrifugal force and the frictional force between the wall of the rotating flask and the sample resulted in the formation of a thin film of warm solvent being spread over a large surface and the solvent is evaporated with the help of vacuum pressure (400 mbar). The residual solvent was then removed at 60° C. for 14 hrs.

The various modifications of the invention, in addition to those mentioned herein, are apparent to those skilled in the art from the foregoing description. Such modifications are also intended to fall within the scope of the appended claims. While the particular embodiments of the present invention have been described, it will be obvious to those skilled in the art that various modifications of the invention can be made without departing from the spirit and scope of the invention.

We claim:

1. A formulation suitable for oral administration comprising: (3,5-Bis trifluoromethyl)-N-[4-methyl-3-(4-pyridin-3-yl-pyrimidin-2-yl-amino)phenyl]benzamide (NRC-AN-019) or a salt thereof;
and at least one polymeric matrix agent, wherein:
the formulation is in the form of a solid dispersion; and
said NRC-AN-019 is present in an amount of about 0.1% to 99.9% by weight relative to the total weight of the composition.

2. The formulation as claimed in claim 1, wherein NRC-AN-019 is in crystalline form.

3. The formulation as claimed in claim 1, wherein NRC-AN-019 is present in an amount of about 0.5% to 30% by weight relative to the total weight of the composition.

4. The formulation as claimed in claim 1, wherein the ratio of NRC-AN-019 to polymer matrix agent is from about 1:1 to about 1:8 in total weight of the composition.

5. The formulation as claimed in claim 1, wherein the at least one polymer matrix agent is an ionic polymer.

6. The formulation as claimed in claim 5, wherein the ionic polymer is selected from a cellulosic polymer, a methacrylic acid copolymer, a carboxyvinyl polymer, a vinyl acetate polymer, and combinations thereof.

7. The formulation as claimed in claim 1, wherein the solid dispersion is obtainable by a process selected from solvent controlled precipitation, solvent evaporation, lyophilisation, pH controlled precipitation, hot melt extrusion and super critical fluid technology.

8. A process for obtaining solid dispersion as claimed in claim 7, wherein the process comprises mixing NRC-AN-019 and the at least one polymeric matrix agent to form a homogeneous, molecularly disperse mixture.

9. The process according to claim 8, wherein the mixing is performed by dissolving NRC-AN-019 and the at least one polymeric matrix agent in an organic solvent, followed by spraying into an anti-solvent and obtaining a co-precipitate of NRC-AN-019 and the at least one polymeric matrix agent.

10. The process according to claim 9, wherein the solvent is selected from dimethylformamide, dimethylacetamide, dimethyl sulfoxide, N-Methyl-2-pyrrolidone and mixtures thereof.

11. The process according to claim 9 wherein the anti-solvent is selected from water, hydrochloric acid, ethyl acetate, toluene, methylene chloride, acetonitrile and mixtures thereof.

12. The formulation as claimed in claim 6, wherein the methacrylic acid copolymer is selected from poly(methacrylic acid, methyl methacrylate), poly(methacrylic acid, ethyl acrylate) and a combination thereof.

13. A method of treating cancer in a patient comprising administering to said patient a therapeutically effective amount of a formulation according to claim 1.

14. The method of claim 13, wherein the cancer is chronic myeloid leukemia, head cancer, neck cancer or prostate cancer.

15. The formulation as claimed in claim 1, wherein NRC-AN-019 is in amorphous form.

16. The formulation as claimed in claim 1, wherein NRC-AN-019 is in a combination of crystalline and amorphous forms.

17. The formulation as claimed in claim 1, wherein the at least one polymer matrix agent is a non-ionic polymer.

18. The formulation as claimed in claim 17, wherein the non-ionic polymer is selected from a cellulosic polymer, polyvinylpyrrolidone, vinyl pyrrolidone vinyl acetate copolymer, polyalkylene glycol and combinations thereof.

19. The formulation as claimed in claim 1, wherein the at least one polymer matrix agent is a combination of an ionic polymer and a non-ionic polymer.

* * * * *